United States Patent
St. Clair et al.

(10) Patent No.: US 8,100,950 B2
(45) Date of Patent: Jan. 24, 2012

(54) OBLIQUE LUMBAR INTERBODY FUSION

(75) Inventors: Selvon St. Clair, Cleveland Heights, OH (US); Isador H. Lieberman, Pepper Pike, OH (US); Mark Kayanja, North Ridgeville, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 718 days.

(21) Appl. No.: 12/178,995

(22) Filed: Jul. 24, 2008

(65) Prior Publication Data

US 2009/0163957 A1    Jun. 25, 2009

Related U.S. Application Data

(60) Provisional application No. 60/962,238, filed on Jul. 27, 2007.

(51) Int. Cl.
*A61B 17/88* (2006.01)
(52) U.S. Cl. .................................................. 606/279
(58) Field of Classification Search .............. 606/246, 606/279, 301, 304, 323, 97, 99, 102, 104, 606/86 A, 130; 623/17.11
See application file for complete search history.

(56) References Cited

U.S. PATENT DOCUMENTS

| 6,725,080 | B2 * | 4/2004 | Melkent et al. | 600/424 |
| 2003/0078495 | A1 * | 4/2003 | Goodwin | 600/424 |
| 2006/0085010 | A1 * | 4/2006 | Lieberman | 606/99 |
| 2006/0111779 | A1 * | 5/2006 | Petersen | 623/17.11 |
| 2006/0224088 | A1 * | 10/2006 | Roche | 600/587 |
| 2006/0235338 | A1 * | 10/2006 | Pacheco | 600/587 |
| 2008/0097436 | A1 * | 4/2008 | Culbert et al. | 606/61 |

OTHER PUBLICATIONS

Grob et al., "Direct Pediculo-Body Fixation in Cases of Spondylolisthesis with Advanced Intervertebral Disc Degeneration", *Eur Spine J*, 1996, 5:281-285.

* cited by examiner

*Primary Examiner* — Eduardo C Robert
*Assistant Examiner* — David Comstock
(74) *Attorney, Agent, or Firm* — Tarolli, Sundheim, Covell & Tummino LLP

(57) ABSTRACT

A method fuses an inferior vertebra and a superior vertebra together. The method includes the steps of: extending a screw obliquely, both anteriorly and superiorly, through the inferior vertebra; and further extending the screw across an interbody space and into the superior vertebra both anteriorly and superiorly.

10 Claims, 1 Drawing Sheet

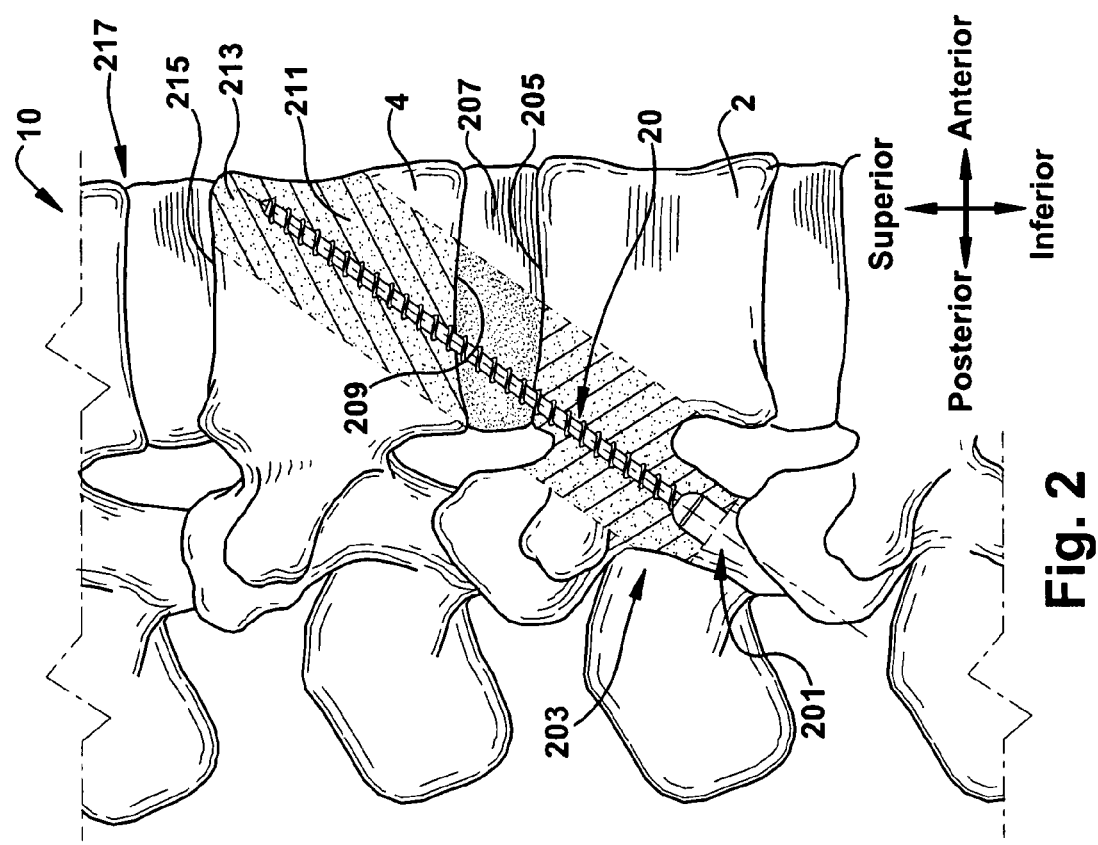
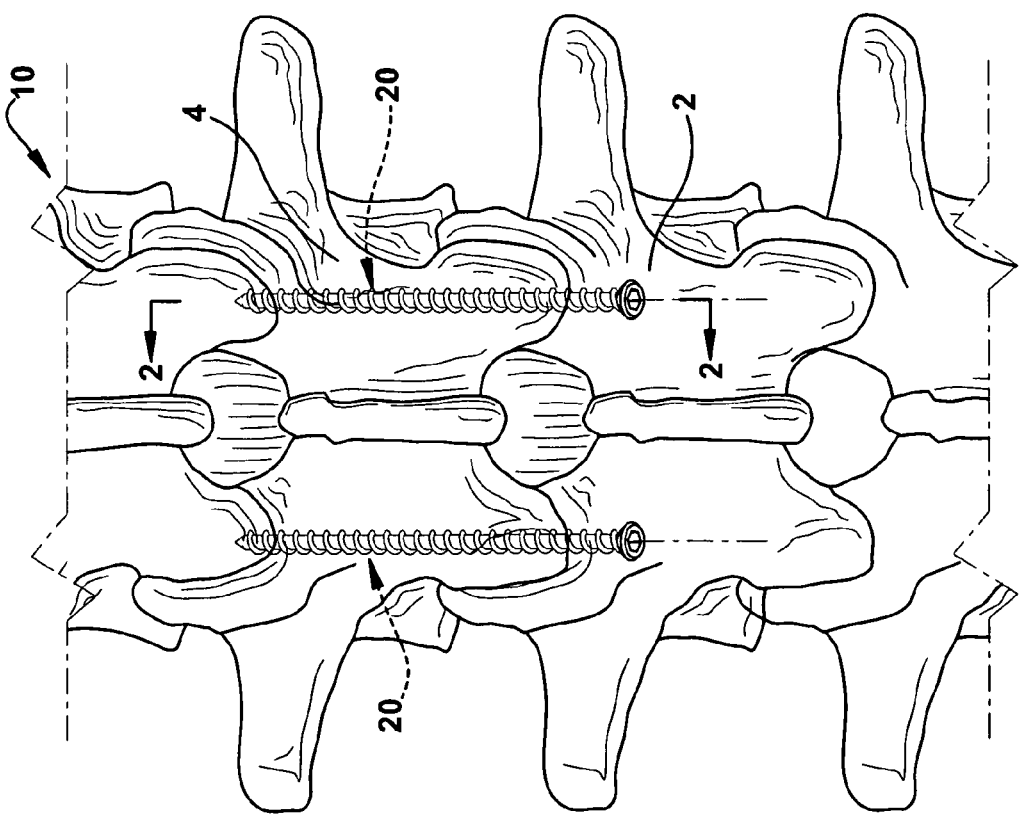

OBLIQUE LUMBAR INTERBODY FUSION

RELATED APPLICATION

This application claims the benefit of U.S. Provisional Patent Application Ser. No. 60/962,238, filed Jul. 27, 2007 which is incorporated herein by reference.

TECHNICAL FIELD

The present invention states that the field of the invention is a minimally invasive method for fusing adjacent vertebrae.

BACKGROUND OF THE INVENTION

Lower back pain is a common condition amongst the adult population and represents the most common cause of loss of work productivity. The aetiology of mechanical lower back pain includes a variety of conditions: 70% from lumbar strain or sprain; 10% from degenerative changes to discs and facets; 4% from herniated discs; 4% from osteoporotic compression fractures; 3% from spinal stenosis; and 1% from other causes (infection, ankylosing, spondylitis, neoplasms, etc.). When non-operative modalities fail, treatment may then require fusion for varied indications that include degenerative disc disease, spondylosis, age-related degeneration of the spine, infection, and primary or metastatic neoplasms. An estimated 350,000 spinal fusion procedures were performed in the US in 2004 at an estimated cost of 1.5-2 billion dollars. Nevertheless, even with new advancement in surgical treatment options, lower back pain still remains a formidable challenge to physicians in the United States. Therefore, the surgeon's task remains to develop and utilize innovative and effective ways of fusing a diseased spine while meeting the goals of surgical spine fusion, including restoration of alignment, halting of neurological progression, and amelioration of pain.

The conventional ventral mini-open retroperitoneal approach to the lower lumbar spine requires an initial incision usually less than 4 cm in length and is normally employed for ventral L4-5 and L5-S1 fusion. This procedure involves dissection through the skin, soft tissue, and the rectus abdominus muscle for access into the retroperitoneal space to expose the ventral lumbar spine. A number of anatomic structures may be injured during this dissection: the ureter; the common iliac arteries and veins and the median sacral vessels. Also, damage to the presacral plexus may result in premature ejaculation in males.

A conventional ventrolateral transpsoas approach has been developed for instrumentation of L1 through L4. With the patient positioned in a 90° lateral decubitus position, the spine is accessed laterally through the psoas muscle. Through this ventrolateral approach, morbidity from dural exposure, excessive nerve root retraction, epidural bleeding, and excessive scarring may occur. Furthermore, injury to the femoral or genito-femoral nerves may occur.

A conventional dorsal approach to the lumbar spine places the patient in a prone position and, through a midline incision over the level of interest, dissects and laterally retracts the dorsal paraspinal muscles. Apart from a significant risk of blood loss, the dural sac and the posterior rami, which lie between the transverse processes lateral to the pars interarticularis and the facet joint capsules, may be injured. Perioperative pain and post-operative scarring are typically encountered following the dorsal approach.

Spinal fusion may be performed without or without a concomitant diskectomy, and the spine may or may not be instrumented. A particular technique used to effect spinal fusion relies both on the pathology in question and the expertise of the surgeon performing the procedure. The conventional gold standard for lumbar segmental spinal fixation is a ventral interbody graft with dorsal pedicle screws. Other conventional forms of fixation include ventral plates/rods with screws and dorsal transfacet fixation.

The vast majority of the approach-related morbidity associated with open instrumented lumbar fusion procedures is caused by extensive soft tissue muscle dissection and prolonged retraction of the soft tissues and muscle. Limited retraction and exposure has been related to improved clinical outcomes with less post-operative pain. Therefore, procedures of shorter duration involving minimal dissection and retraction are desirable.

Minimally invasive approaches to lumbar spine fixation may advantageously produce decreased morbidity, limited postoperative in-patient stay, decreased cost, and the potential to improve long-term outcomes. Improved forms of instrumentation have been developed to take advantage of various access corridors to the spine, such as percutaneous introduction of pedicle screws and rods. Development of minimally invasive ventral access corridors to the lumbar spine has lagged behind dorsal access. Expandable tube retractors to allow direct visualization have been developed to assist surgeons. Navigation systems also may serve as aids for the accurate placement of pedicle screws.

Further advances in minimally invasive lumbar fixation may involve the development of a segmental lumbar fusion technique that, when used alone, eliminates the need for dorsal incisions. This technique is only available for the L5-S1 spine segment.

Thus, minimally invasive techniques (to manage pathologic conditions in various surgical disciplines) may be successfully and reliably performed. Although the treatment of lumbar disc diseases via minimally invasive approaches is rapidly gaining acceptance, minimally invasive lumbar fusion procedures have only recently been developed and implemented. For example, a conventional axial lumbar interbody fusion/fixation uses a percutaneous pre-sacral approach for safely and effectively fusing the L5-S1 vertebral segment. There is therefore a need in the art for an improved spinal fixation apparatus and method that utilizes a minimally invasive approach with the inherent advantage of reduction in approach-related morbidity associated with conventional lumbar fusion.

SUMMARY OF THE INVENTION

A method in accordance with the present invention fuses an inferior vertebra and a superior vertebra together. The method includes the steps of: extending a screw obliquely, both anteriorly and superiorly, through the inferior vertebra; and further extending the screw across an interbody space and into the superior vertebra both anteriorly and superiorly.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic view of a method in accordance with the present invention; and FIG. 2 is a schematic sectional view taken along lines 2-2 in FIG. 1.

DESCRIPTION OF EXAMPLE EMBODIMENT

A method 10 in accordance with the present invention defines a minimally invasive and reliable placement of spinal fusion implants between adjacent vertebrae to facilitate rigid fixation. The method 10 is percutaneously applied to interbody vertebral fixation at and above the L5-S1 vertebral segment. The method 10 is applied as an outpatient procedure for vertebral body fixation and will thus cost less than conventional invasive surgical approaches, which requires a minimum of 3-5 days stay in the hospital.

As shown in FIGS. 1 & 2, the method 10 comprises percutaneous lumbar interbody screw fixation of two partially threaded cancellous screws 20 inserted into adjacent lumbar vertebrae 2, 4 following a diskectomy, also performed with percutaneous tools. The diskectomy is performed through a lateral extraforaminal approach using percutaneous tools. Then, an interbody graft placement and screw insertion is performed. As shown in FIG. 2, the trajectory of the screws 20 is: (i) from the inferior articular process 201 of the facet joint (ii); traversing the pedicle 203; (iii) through the superior endplate 205 of the inferior vertebra 2; (iv) across the interbody space 207; (v) through the inferior endplate 209 of the superior vertebra 4; (vi) through the centrum 211 of the superior vertebra; and (vii) to the junction 213 of the superior endplate 217 of the superior vertebra with the anterior vertebral wall 217.

The method 10 provides for rigid interbody vertebral fixation via a percutaneous approach. This method 10 uses a pedicle screw device and delivery system as a stand alone device or in combination with anterior lumbar interbody fusion to facilitate a stable fusion between vertebrae segments. The method 10 further provides a method for percutaneous intervetebral disc removal, prior to a fusion procedure or for a diagnostic biopsy. The method 10 also provides percutaneous preparation and fixation of facet joints for fusion. The method 10 includes percutaneous screw insertion with two partially threaded cancellous screws 20 inserted obliquely through two adjacent lumbar vertebrae 2, 4. As shown in FIG. 2, the screws 20 extend in an inclined, or slanted, manner such that the screws are angled between the superior and anterior directions.

The method 10 provides a completely percutaneous and rod-less oblique interbody screw fixation system for transfixing lumbar vertebrae segments at and above the L5-S1 level. The method 10 precisely defines a screw trajectory using fluoroscopy for the oblique insertion of guide wire-assisted interbody screws 20 across an interbody joint. The screws 20 traverses the pedicle 203 of the caudal vertebra 2, the interbody space 207, the inferior endplate 209, and centrum 211 of the cephalad vertebra 4, and terminate at the junction 213 of the superior end plate 215 and ventral cortex 213 of the cephalad vertebra. The method 10 makes further use of facet fixation mapping using similar techniques.

The method 10 employs a dorsal approach (from posterior to anterior) to the spine with the patient in the prone position. The level of approach is confirmed with anteroposterior and lateral fluoroscopy. The midline, as seen in FIG. 1, is identified and marked with an indelible marker. Paramedian lines are then drawn on the skin 4 to 5 cm offset from the midline. Under lateral fluoroscopy, a spinal needle, such as a 22-gauge needle, is inserted through the paramedian lines and advanced until its trajectory bisects an inferior junction of the caudal pedicle 203 and transverse process 201. Antero-posterior fluoroscopy (not shown) then confirms the medial-lateral position of the needle that should engage the lateral cortical rim of the pedicle 203.

Under fluoroscopic guidance, the spinal needle is obliquely advanced into the pedicle 203 from caudal to rostral with care taken not to violate the intertransverse fascia. Safe placement requires the obtaining of sequential, biplanar fluoroscopic images until the tip of the needle lies at the 2-3 mm ventral to the junction 213 of the superior endplate 215 and dorsal vertebral body line 217. Eventual K-wire placement is safely provided such that the medial pedicle wall, and the dorsal edge of the superior endplate 215 of same vertebra, have not been breached at this junction 213 as determined by antero-posterior fluoroscopy. A K-wire is then placed through the needle, which may subsequently be removed. The K-wire is then advanced under lateral fluoroscopic guidance through the disc and inferior endplate of the rostral vertebra until 2-3 mm dorsal to the ipsilateral junction 213 of the superior endplate 215 and the ventral body line 217. Antero-posterior fluoroscopy then confirms the medial-lateral position of the oblique interbody vertebral fixation.

Under fluoroscopic guidance, skin incisions are made using a scalpel. This is followed with a trochar and cannula to open up the screw track through the soft tissues. A Jamshidi needle is then docked on the spine at the appropriate location (L2 for L1-2, L3 for L2-3, L4 for L3-4, L5 for L4-5 and S1 for L5-S1) and the trajectory adjusted, under fluoroscopy, to ensure entry at the inferior junction of the pedicle and transverse process, and termination at the junction between the ventral cortical wall and the superior endplate. The cortex is opened to make way for the K-wire, which is then inserted along the oblique interbody screw trajectory. Using standard equipment and fluoroscopy, the K-wire is advanced under lateral fluoroscopic guidance from the inferior junction of the caudal pedicle 203 and transverse process 201 through the intervertebral disc, inferior endplate 209 of the cephalad vertebra 4, stopping just short of the ipsilateral junction 213 of the superior endplate 215 and ventral body line 217.

Antero-posterior fluoroscopy then confirms the mediallateral position of the oblique interbody screw 20. This trajectory traverses the pedicle 203 of the caudal vertebra 2, the interbody space 207, the inferior endplate 209 and centrum 211 of the cephalad vertebra 4, and terminate at the junction 213 of the superior end plate 215 and ventral cortex 217 of the cephalad vertebra. The trajectory is shown in FIG. 2.

For transfacet fixation, before a surgical incision, a level of approach is confirmed with antero-posterior and lateral fluoroscopy. The midline is identified and marked. Paramedian lines are then drawn 4 to 5 cm off midline. Under lateral fluoroscopy, an 11-gauge spinal needle is inserted lateral and collinear to the transverse process, through the paramedian lines and advanced until its trajectory bisects the posterior junction of the superior articulating facet and the transverse process. Antero-posterior fluoroscopy then confirms the medial-lateral position of the needles that should just engage the lateral cortical rim of the superior articulating process.

Under fluoroscopic guidance, the spinal needle is obliquely advanced into the superior articulating process from caudal to rostral until the inner cortex/cartilage border. A K-wire is then placed through the needle, which is subsequently removed. The K-wire is then advanced under lateral fluoroscopic guidance through the facet-joint space, cartilage/inner (lateral) cortex of the inferior articulating facet until the medial (outer) wall of that facet, without violating that cortex. Antero-posterior fluoroscopy then confirms the mediallateral position of collinear facet fixation.

For facet joint fixation, the K-wire is obliquely (45-55°) advanced from the dorsal junction of the superior articulating facet and the transverse process into the superior articulating process, from caudal to cephalad, through the facet joint space, cartilage/inner (lateral) cortex of inferior articulating facet until the medial (outer) wall of that facet without violating this cortex. Antero-posterior fluoroscopy then confirms the medial-lateral position of the collinear facet fixation.

The method 10 provides a screw 20 with a trajectory from the lateral junction of the pedicle 203 and transverse process, of the inferior vertebra 2, diagonally (when viewed as in FIG. 2) traversing the pedicle, through the superior endplate 205 of the inferior vertebra, across the interbody space 207, through the inferior endplate 209 of the superior vertebra 4, through the centrum 211 of the superior vertebra, and to the junction 213 of the superior endplate 215 of the superior vertebra with the anterior vertebral wall 217.

The screw 20 is inserted through a cannula and is self-tapping with a blunt end to prevent penetration of vascular structures. The screw 20 may have two diameters (not shown): a larger, diameter for purchase distally in the inferior vertebra 2 (pedicle and vertebral body) and a smaller diameter for purchase proximally in the superior vertebra 4 with the diameters interlocking concentrically. The screw 20 may further have polyaxial head (not shown) with an attached plate through which a transfacet screw can be inserted. The range of diameters may be varied to allow for different pedicle sizes. The screw 20 may be made of stainless steel or titanium.

The method 10 may be employed in conjunction with an anterior interbody fusion with bone graft, through which the screw 20 may pass. The method 10 may be performed completely percutaneously or as a mini-open approach/procedure. The method 10 may be utilized to fuse the T12/L1, L1/L2, L2/L3, L3/L4, L4/L5 and L5/S1 vertebral segments.

From the above description of the invention, those skilled in the art will perceive improvements, changes and modifications. Such improvements, changes, and modifications within the skill of the art are intended to be covered by the appended claims.

Having described the invention, the following is claimed:

1. A method for fusing an inferior vertebra and a superior vertebra together, said method comprising the steps of:
   extending a screw obliquely, both anteriorly and superiorly, through the inferior vertebra;
   further extending the screw across an interbody space and into the superior vertebra both anteriorly and superiorly; and
   defining a trajectory for the screw utilizing fluoroscopic imaging;
   wherein said method is performed percutaneously on a non-spondylolisthetic subject.

2. The method as set forth in claim 1 further including the step of inserting and mounting the screw to the inferior and superior vertebrae entirely through a cannula.

3. The method as set forth in claim 1 further including the steps of traversing a pedicle of the inferior vertebra with the screw and extending the screw through a superior endplate of the inferior vertebra.

4. The method as set forth in claim 3 further including the step of further extending the screw through an inferior endplate of the superior vertebra and through a centrum of the superior vertebra.

5. The method as set forth in claim 4 further including the step of further extending the screw to a junction of a superior endplate of the superior vertebra and an anterior vertebral wall.

6. The method as set forth in claim 1 further including the step of extending the screw through a pedicle of a posterior portion of the inferior vertebra, through a superior endplate of the inferior vertebra, across the interbody space, through an inferior endplate of the superior vertebra, through a centrum of the superior vertebra, and to a junction of a superior endplate of the superior vertebra with a anterior vertebral wall.

7. The method as set forth in claim 1 further including the step of guiding the screw across the interbody space between the inferior vertebra and the superior vertebra with at least one wire.

8. The method as set forth in claim 1 further including the step of extending the screw at an angle between 45-55 degrees relative to a longitudinal axis defined by the inferior and superior vertebrae.

9. The method as set forth in claim 1 further including the steps of:
   extending a second screw obliquely, both anteriorly and superiorly, through the inferior vertebra, the second screw extending on a lateral side of a spine extending through the inferior and superior vertebrae other than a side of the first screw; and
   further extending the second screw across the interbody space and into the superior vertebra both anteriorly and superiorly.

10. A method for fusing an inferior vertebra and a superior vertebra together, said method comprising the steps of:
   extending a screw obliquely, both anteriorly and superiorly, through the inferior vertebra;
   further extending the screw across an interbody space and into the superior vertebra both anteriorly and superiorly; and
   defining a trajectory for the screw utilizing either of a robotic and a navigation system;
   wherein said method is performed percutaneously on a non-spondylolisthetic subject.

* * * * *